United States Patent

Pavone et al.

Patent Number: 6,075,006
Date of Patent: Jun. 13, 2000

[54] SOLUBLE TACHYKININ ANTAGONISTS, THE PREPARATION AND USE THEREOF

[75] Inventors: Vincenzo Pavone; Angelina Lombardi; Carlo Pedone; Mario De Rosa; Mosé Rossi, all of Naples, Italy

[73] Assignee: Centro Interuniversitario di Ricera Sui Peptidi Bioattivi-Universita' Degli Studi di Napoli Federico II, Naples, Italy

[21] Appl. No.: 09/125,542

[22] PCT Filed: Feb. 26, 1997

[86] PCT No.: PCT/EP97/00917

§ 371 Date: Aug. 28, 1998

§ 102(e) Date: Aug. 28, 1998

[87] PCT Pub. No.: WO97/31941

PCT Pub. Date: Sep. 4, 1997

[30] Foreign Application Priority Data

Mar. 1, 1996 [IT] Italy ................. MI96A0401

[51] Int. Cl.[7] ............ A61K 38/12; A61K 38/14; C07K 7/56; C07K 9/00
[52] U.S. Cl. .................. 514/8; 514/10; 530/317; 530/321; 530/322
[58] Field of Search .................. 514/9, 10, 11, 514/17, 8; 530/317, 318, 321, 329, 322

[56] References Cited

FOREIGN PATENT DOCUMENTS

WO 93/03059 2/1993 WIPO .
WO 93/21227 10/1993 WIPO .

OTHER PUBLICATIONS

By A.T. McKnight et al., "Pharmacological specificity of novel, synthetic, cyclic peptides as antagonists at tachykinin receptors", *British Journal of Pharmacology*, vol. 104, 1991, pp. 355–360.

By G. Holzemann et al., "Cyclic hexapeptide NK–2 antagonists", *International Journal of Peptide and Protein Research*, vol. 44, 1994, pp. 105–111.

By C.A. Maggi et al., "Men 10,627, a Novel Polycyclic Peptide Antagonist of Tachykinin NK2 Receptors", *Journal of Pharmacology and Experimental Therapeutics*, vol. 271, No. 3, 1994, pp. 1489–1500.

By V. Pavone et al., Design and structure of a novel Neurokinin A receptor antagonist cyclo(-Met$^1$-Asp$^2$-Trp$^3$-Phe$^4$-Dap$^5$-Leu$^6$-)cyclo (2β–5β), *Journal of the Chemical Society Perkin Transactions 2*, 1995, pp. 987–993.

*Primary Examiner*—Jeffrey E. Russel
*Attorney, Agent, or Firm*—Young & Thompson

[57] ABSTRACT

The compounds of formula (I) cyclo[$X_1^1$—$Z_1^2$—$X_2^3$—$X_3^4$—$Z_2^5$—$X_4^6$]cyclo(2β–5β) wherein: $X_1$=(D or L)Cys(Y) or (D or L)SeCys(Y), $Z_1$=Asp and $Z_2$=Dap or $Z_1$=Dap and $Z_2$=Asp and $X_2$, $X_3$ and $X_4$=natural or synthetic hydrophobic amino acids, having $Z_1$, $Z_2$, $X_2$, $X_3$ and $X_4$ the same D or L configuration; Y=is a glycosidic group selected from the aldo and keto hexoses in the furanose or pyranose form bound to the cysteine with an α or β thioacetalic bond or a cyclithol or a polyvinyl alcohol or PEG, constituted of 5 to 10 monomeric unities, bound to the cysteine with a thioether bond, are endowed of high solubility and of potent tachykinin-antagonistic activity.

3 Claims, No Drawings

SOLUBLE TACHYKININ ANTAGONISTS, THE PREPARATION AND USE THEREOF

The present invention refers to soluble tachykinin antagonists, to their preparation and to pharmaceutical compositions containing them.

Many tachykinin antagonists are known in literature and among these the monocycle (A. T. McKnight et al., Br. J. Pharmacol. 1991, 41,376) and bicycle (V. Pavone et al., J. Chem. Soc. Perkin Trans 2, 1995, 987) compounds are particularly interesting. All the compounds developed up to now are characterized by a high hydrophobicity and therefore are all water insoluble. In fact patent WO 93/21227 discloses insoluble bicycle peptide tachykinin antagonists, wherein all the claimed structures are characterized by amino acids with hydrophobic side chains or if the chains are polar, they are functionalized so as to confer hydrophobicity to the functional group. The low water solubility (no more than 15 μg/ml) which inevitably characterizes these extremely hydrophobic compounds, has effectively hampered any possible pharmacological applications of such molecules up to now, notwithstanding their in vitro interesting biological activity. It is likewise known from literature (L. Quartara et al., J. Med. Chem. 1994, 37, 3630) that an increase in the hydrophilicity of this class of molecules causes a progressive reduction in their biological activity. From this reference point, the pharmaceutical industry's interest comes out in the search for new classes of tachykinin-antagonists of the water soluble type, but with a highly specific activity.

The present invention discloses tachykinin-antagonists which at the same time present a high water solubility and a high biologic activity. The compounds of the invention have the following general formula (I): cyclo[$X_1^1$—$Z_1^2$—$X_2^3$—$X_3^4$—$Z_2^5$—$X_4^6$]cyclo(2β–5β) wherein: $X_1$=(D or L)Cys(Y) or (D or L)SeCys(Y), $Z_1$=Asp and $Z_2$=Dap or $Z_1$=Dap and $Z_2$=Asp and $X_2$, $X_3$ and $X_4$=natural or synthetic hydrophobic amino acids, having $Z_1$, $Z_2$, $X_2$, $X_3$ and $X_4$ the same D or L configuration; Y=is a glycosidic group selected from the aldo and keto hexoses in the furanose or pyranose form bound to the cysteine or to the selenocysteine with an α or β thio- or seleno-acetal bond or a cyclithol or a polyvinyl alcohol or PEG, constituted of 5 to 10 monomeric unities, bound to the cysteine or to the seleno cysteine respectively with a thio- or seleno-ether bond.

The compounds with $X_2$=Trp or 1-Nal; $X_3$=Phe and $X_4$=Leu or Cha are particularly preferred.

The compounds of formula (I) have many chiral centres, and therefore the invention comprises all the possible enantiomers.

The compounds of formula (I) show unique structural characteristics, which differentiate them from the known products. In fact, the claimed compounds, contrary to those reported up to now (A. T. McKnight et al., Br. J. Pharmacol. 1991, 41, 376; C. A. Maggi et al., J. Pharmacol. and Expt. Therapeutics, 1994, 271, 1489), contain highly hydrophilic functional groups, which give them an at least 100 times higher water solubility. The high water solubility and the strong pharmacological activity, higher than that of the insoluble compounds previously developed, make this new class of molecules ideal for the development of a wide set of pharmaceutical formulations. As far as these applicative aspects are concerned, the compounds of the invention substantially differ from the insoluble derivatives previously studied in that the latter do not permit the development of pharmaceutical compositions which can be used therapeutically.

In particular, the compounds of formula I characterized by a residue of cysteine or of selenocysteine, whose respective —SH or —SeH group is involved in a thio- or seleno-glycosidic or thio- or seleno-ether bond with a galactose, glucose, inositol or PEG residue or low molecular weight polyalcohols, even though with high water solubility, they have an activity even a little higher than the activity of the best antagonists of the insoluble type, such as the MEN 10627 compound (C. A. Maggi et al., J. Pharmacol. and Expt. Therapeutics, 1994, 271, 1489), which has a solubility of only 15 μg/ml. This is even more surprising if it is considered that up to now the data available in literature showed that when the water solubility increases inevitably the pharmacological activity of such compounds decreases (L. Quartara et al., J. Med. Chem. 1994, 37, 3630).

The compounds of formula (I) behave in a surprising opposite manner with respect to the analogues wherein cysteine functionalized with β-D-galactose has been substituted with the following residues:

Asn(β-D-gal): Gln(β-D-gal); Ser(β-D-gal); hSer(β-D-gal); hCys(β-D-gal).

In particular, the analogues with Asn(β-D-gal) and Ser(β-D-gal) were synthesized for comparison and the solubility and biologic activity are reported in the example 2.

The compounds of formula (I), which are the object of the present invention, can be synthesized according to the different techniques known from literature, e.g. Schroeder et al. "The Peptides" vol. 1, Academic. Press., 1965; Bodanszky et al. "Peptide Synthesis" Interscience Publischer, 1966; Barany & Merrifield, "The peptides; Analysis, Synthesis, Biology", 2, Chapter 1, Academic. Press., 1980. These techniques include the peptide-solid phase synthesis, the peptide synthesis in solution, the synthetic methods of the organic chemistry, or any combination thereof. The chosen synthetic scheme will obviously depend on the composition of the particular molecule. Since all of the claimed molecules are peptides, synthetic methods based on appropriate combinations of solid phase techniques and the classic methods in solution are preferably used, which involve low costs of production particularly in an industrial scale. In details such methods consist in:

i) the synthesis in solution of fragments of the peptide chain through the sequential coupling of the N-protected amino acids, appropriately activated, with an amino acid or with a C-protected peptide chain, with isolation of the intermediates, following selective deprotection of the N and C terminals of said fragments and their coupling till the preparation of the desired peptide. Finally the groups involved in the cyclizations, for instance the N and C terminals or the side chains, are selectively deprotected and afterwards are condensed. Finally, if necessary, the side chains are deprotected.

ii) The solid phase synthesis of the peptide chain from the C-terminal to the N-terminal on an insoluble polymeric support, the cyclization in solid phase between the side chains previously deprotected. The peptide is removed from the resin through the hydrolysis with anhydrous hydrofluoric acid or with trifluoroacetic acid in the presence of suitable scavengers and then the cyclization of the monocyclic peptide is carried out in diluted solution. Then the side chains are deprotected.

Fmoc-Cys(β-D-Gal(Ac)4)-OH, Fmoc-Ser(β-D-Gal(Ac)4)-OH, Fmoc-Asn(β-D-Gal)-OH, can be obtained according to the methods known in literature (M. Gerz, et al., Angew. Chem. Int. Ed. Engl., 1993, 32, 269; Kessler, H. et al. J. Am. Chem. Soc. 1992, 114, 4805; Kessler H. et al., J. Am. Chem. Soc. 1991, 113, 7550).

The seleno-derivatives are obtained with similar procedures starting from the selenocysteine, using the known techniques for the protection of the amino function.

The above indicated compounds of formula (I) resulted in more potent antagonists than other analogous antagonists and thus they can be administered in amounts lower than those required for the known products.

Thus these compounds are suitable for the therapeutic administration to the superior animals and to humans. In fact their water solubility allows to prepare simple and unexpensive pharmaceutical preparations, suitable for the parenteral, oral, inhalatory and sublingual administrations, while their high biologic activity allows to obtain effective pharmacological effects even with low amounts. Examples of suitable formulations comprise capsules, tablets, syrups, solutions or sterile injectable lyophils, aerosols.

The compounds of the invention can be administered in amounts comprised between 0.01 mg/Kg and 10 mg/Kg for the treatment of arthritis, asthma, inflammation, tumoral growth, gastro intestinal hypermotility, Huntington disease, neuritis, neuralgia, migraine, hypertension, incontinence of urine, urticaria, symptoms of the carcinoid syndrome, influenza and cold.

The following examples which are not limitative further illustrate the compounds of the invention.

List of the Abbreviations

The nomenclature and abbreviations of the amino acids are consistent with the recommendations of the IUPAC-IUB Joint Commission on Biochemical nomenclature (Eur. J. Biochem. 1984, 138:9); the amino acids are meant in the L configuration if not otherwise specified. The other abbreviations are: NKA=neurokinin A; SP=substance P; Dap=2,3-diaminopropionic acid; SeCys=selenocysteine; PEG=polyethylene glycol; 1-Nal=1-naphthyl-alanine; Cha=cyclohexylalanine; gal=galactose; hSer=homoserine; hCys=homocysteine; Boc=tert-butyloxycarbonyl; PAM=phenylacetamidomethyl; Fmoc=9-fluorenylmethyloxycarbonyl; PyBop=benzotriazol-1-yl-oxypyrrolidinephosphonium hexafluorophosphate; DIEA=diisopropylethylamine; Fm=fluorenylmethyl; DCC=dicyclohexylcarbodiimide; DMF=N-N' dimethylformamide; DCM=dichloromethane; i-PrOH=isopropanol; Ac=acetyl; DMS=dimethylsulfur; MeOH=methanol; Rt=retention time; FAB-MS=fast atom bombardment mass spectrometry; HPLC=high pressure liquid chromatography; HOBt=1-hydroxybenzotriazole; TFA=trifluoroacetic acid.

EXAMPLE 1

A) Preparation of the compound of general formula I wherein $X_1$=Cys($\beta$-D-Gal); $Z_1$=Asp; $X_2$=Trp; $X_3$=Phe; $Z_2$=Dap; $X_4$=Leu {cyclo[Cys$^1$($\beta$-D-Gal)-Asp$^2$-Trp$^3$-Phe$^4$-Dap$^5$-Leu$^6$]cyclo(2$\beta$–5$\beta$)}(SEQ ID NO:1).

The peptide was assembled in solid phase, through Boc chemistry, on a PAM resin functionalized with Boc-Leu, using a ABI 430A Applied Biosystem synthesizer. The standard deprotection and coupling cycles were used. The following amino acids were coupled in the order with 0.651 g of Boc-Leu-PAM resin (scale 0.5 mmol): Boc-Dap(Fmoc)-OH (1.5 mmol; PyBop 1.5 mmol, DIEA 3 mmol); Boc-Phe-OH, Boc-Trp(CHO)-OH and Boc-Asp(OFm)-OH (2 mmol and DCC/HOBt as the coupling agent). Before carrying out the cyclization between the $\beta$-carbonyl of Asp and the $\beta$-amino group of Dap, the side chains of the two amino acids were deprotected using two deprotection cycles with a solution 20% piperidine in DMF of 3 and 7 min respectively. Repeated washings were then carried out with the following solvents: DCM, DMF, DCM, and i-PrOH. The cyclization was carried out adding PyBop (1.5 mmol) and DIEA (3 mmol) to the suspended resin in 15 ml of DMF. The solution was reacted overnight. Afterwards washing cycles were carried out using DMF and DCM. After the Asp amino group deprotection, Fmoc-Cys($\beta$-D-Gal(Ac)4)-OH (1.5 mmol) was coupled to the monocyclic peptide using PyBop as coupling agent (0.78 g, 1.5 mmol) and DIEA (3 mmol) as the base. The reaction was carried out overnight. The Cys-Fmoc group deprotection was carried out as described for the side chains of Dap and Asp. The removal of the monocyclic peptide from the resin was carried out according to the low/high HF procedure described by Tam & Merrifield (HF/DMS/p-thiocresol/p-cresol 2.5/6.5/0.5/0.5; 4 h at 0° C., followed by HF/p-cresol 9/1; 30 min at 0° C. 362 mg of crude product were recovered (67% yield), which were purified by preparative HPLC yielding 100 mg of pure product (20% yield), in accordance with the analytical HPLC (Rt=17.7 min; purity>99%). 48 mg of PyBop (1 eq.) and 46 $\mu$l of DIEA (3 eq.) pH 8–8.5 were added to 100 mg of the peptide (3) (0.0926 mmol) which were dissolved in 93 ml of DMF (1 mM). The solution was reacted overnight, the completeness of the reaction was determined by analytical HPLC. After eliminating DMF, the sample was dissolved in CHCl$_3$ and extracted two times with a saturated NaHCO$_3$ solution and two times with water. The organic phase was dried over Na$_2$SO$_4$ and the solvent was removed under vacuum. The crude material was redissolved in CH$_3$CN/water and lyophilized. 85.1 mg (87%), HPLC (Rt=19.9 min; purity>88%) were obtained. CH$_3$ONa (1 eq; 346 $\mu$l of a solution containing 5 mg/ml of Na in MeOH) was added to a solution containing 80 mg of (4) (0.0753 mmol) in 64 ml of anhydrous MeOH (1.25 mg peptide/ml MeOH). The reaction was completed in 90 min and the progress was controlled through analytic HPLC. The solution was dried and the product purified by preparative HPLC. The crude product showed a single peak (Rt=14.9 min; area>80%). After purification on preparative HPLC, 29.6 mg with Rt=14.9 min (purity>94%) were obtained. The FAB-MS shows the presence of the molecular ion MH$^+$=895 amu, corresponding to the desired product.

Comparative Example 1

Preparation of the compound of general formula (I) wherein $X_1$=Ser($\beta$-D-Gal); $Z_1$=Asp; $X_2$=Trp; $X_3$=Phe; $Z_2$=Dap; $X_4$=Leu {cyclo[Ser$^1$($\beta$-D-Gal)-Asp$^2$-Trp$^3$-Phe$^4$-Dap$^5$-Leu$^6$]cyclo(2$\beta$–5$\beta$) (SEQ ID NO:2).

The peptide was assembled in solid phase, through the Boc chemistry according to a procedure identical to the procedure for the cyclo[Cys$^1$($\beta$-D-Gal)-Asp$^2$-Trp$^3$-Phe$^4$-Dap$^5$-Leu$^6$)cyclo(2$\beta$–5$\beta$) compound (SEQ ID NO:1), using Fmoc-Ser$^1$ ($\beta$-D-Gal-(Ac)$_4$)-OH instead of Fmoc-Cys$^1$($\beta$-D-Gal(Ac)$_4$)-OH. The bicyclic crude product showed a single peak (Rt=14.0 min; purity>85%). After purification on preparative HPLC 31 mg were obtained with Rt=14.0 min (purity>94%). The FAB-MS analysis shows the presence of the molecular ion MH$^+$=879 amu, corresponding to the desired compound.

Comparative Example 2

Preparation of the compound of general formula I wherein $X_1$=Asn($\beta$-D-Gal); $Z_1$=Asp; $X_2$=Trp; $X_3$=Phe; $Z_2$=Dap; X4=Leu {cyclo[Asn$^1$($\beta$-D-Gal)-Asp$^2$-Trp$^3$-Phe$^4$-Dap$^5$-Leu$^6$]cyclo(2$\beta$–5$\beta$)) (SEQ ID NO:3).

The peptide was assembled in solid phase, through the Fmoc chemistry, on a Macrosorb SPR resin functionalized with the p-hydroxymethylbenzoic acid, a base labile linker, using a Milligen 9010 synthesizer. The standard deprotection and coupling cycles were used.

The esterification of the first residue was carried out with 0.6 mmol (triple excess) of (Fmoc-Leu)$_2$O in DMF. The coupling of Fmoc-Dap(Boc)-OH, Fmoc-Phe-OH, Fmoc-Trp-OH and Fmoc-Asp(OtBu)-OH was carried out with 0.8 mmol of the amino acid and HOBT/DCC as the activating agent. Before carrying out the cyclization between the β-carbonyl of Asp and the β-amino group of Dap, the deprotection of the two amino acidic side chains was carried out with a solution TFA/H$_2$O (90:10). The cyclization was performed by adding HOBt/DCC (1.6 mmol) to the resin suspended in DMF. The reaction was carried out overnight. After the Asp-amino group deprotection, Fmoc-Asn(β-D-Gal)-OH (0.8 mmol) was coupled to the peptide using PyBop (0.8 mmol) as the coupling agent and DIEA (1.2 mmol) as the base. The reaction was carried out overnight. The removal of the monocyclic peptide from the resin was carried out by adding 10 ml of a 1 M NaOH solution to 1 g of peptidyl-resin at 4° C. The reaction was effected for 15 min at room temperature. The solution was filtered, and the filtrate was collected into a beaker containing 10 ml of an aqueous solution of 10% acetic acid. The resin was washed with water and the pH of the filtrate adjusted at 7 with acetic acid. 48 mg of PyBop (1 eq.) and 46 μl of DIEA (3 eq.) were added to 0.1 mmol of the peptide (3) dissolved in 93 ml of DMF (1 mM), keeping the pH between 8 and 8.5. The solution was reacted overnight, the progress of the reaction was determined through analytic HPLC. The solution was dried and the product purified with preparative HPLC. The crude product showed a single peak (Rt=13.5 min; purity>80%). After purification on preparative HPLC, 25 mg with Rt=13.5 min (purity>94%) were obtained. The FAB-MS analysis shows the presence of the molecular ion MH$^+$=992 amu, corresponding to the desired compound.

EXAMPLE 2

In vitro Biologic Activity

The capability of the products of the present invention of acting as antagonists of the neurokinin A receptor was evaluated using a preparation in which the biologic response produced by tachykinins and by the correlated peptides is determined exclusively by the neurokinin A receptor (NK-2 receptor). The deferent conduit, which is contracted by the tachykinins in a dose-dependent manner, was used as the experimental model. The determination of the peptide activity was carried out using a concentration of β-Ala$^8$-NKA [4–10] (3 nM), as the agonist, which produces a response equal to 45% of the highest response. The activity of the peptides described in the example 1 was evaluated for the inhibition of the response to the agonist, as a function of the concentration, and compared to the insoluble MEN-10627 compound (V. Pavone et al., J. Peptide Science 1, 236). The table reports the values of pA2 and the solubility of the compounds.

| Compound | pA$_2$ | Solubility μg/ml |
|---|---|---|
| Example 1 | 8.4 | 1.800 |
| Comparative example 1 | 6.2 | 2.020 |
| Comparative example 2 | 5.8 | 1.980 |
| MEN 10627 | 8.1 | 15 |

What is claimed is:

1. Compounds of general formula (I) cyclo[$X_1^1$—$Z_1^2$—$X_2^3$—$X_3^4$—$Z_2^5$—$X_4^6$]cyclo(2β–5β) wherein: $X_1$=(D or L)Cys(Y) or (D or L)SeCys(Y), $Z_1$=Asp and $Z_2$=Dap or $Z_1$=Dap and $Z_2$=Asp and $X_2$, $X_3$ and $X_4$=natural or synthetic hydrophobic amino acids, having $Z_1$, $Z_2$, $X_2$, $X_3$ and $X_4$ the same D or L configuration; Y=is a glycosidic group selected from the aldo and keto hexoses in the furanose or pyranose form, bound to the cysteine through an α or β thioacetalic bond or a cyclithol or a polyvinyl alcohol or PEG, constituted by 5 to 10 monomeric units, bound to the cysteine with a thioether bond.

2. Compounds according to claim 1 wherein: $X_1$=(D or L)Cys(Y) or (D or L)SeCys(Y), $Z_1$=Asp and $Z_2$=Dap or $Z_1$=Dap and $Z_2$=Asp and $X_2$=Trp or 1-Nal, $X_3$=Phe and $X_4$=Leu or Cha, having $Z_1$, $Z_2$, $X_2$, $X_3$, and $X_4$ the same D or L configuration and Y=being defined as in claim 1.

3. Pharmaceutical compositions containing a compound of claim 1, mixed with a suitable vehicle.

* * * * *